(12) United States Patent
Grace

(10) Patent No.: US 7,077,813 B2
(45) Date of Patent: Jul. 18, 2006

(54) SYSTEM AND METHOD FOR IMPLEMENTING POSTURAL REALIGNMENT PROGRAMS

(76) Inventor: Kathleen J. Grace, 6697 Calle Ponte Bella, Rancho Santa Fe, CA (US) 92091

(*) Notice: Subject to any disclaimer, the term of this patent is extended or adjusted under 35 U.S.C. 154(b) by 331 days.

(21) Appl. No.: 10/454,799

(22) Filed: Jun. 4, 2003

(65) Prior Publication Data
US 2004/0249313 A1 Dec. 9, 2004

(51) Int. Cl.
*A61B 5/117* (2006.01)
*A61B 5/103* (2006.01)

(52) U.S. Cl. .................................. 600/594

(58) Field of Classification Search ............. 600/594, 600/592; 128/898; 482/6; 428/8; 601/23
See application file for complete search history.

(56) References Cited

U.S. PATENT DOCUMENTS

| | | | |
|---|---|---|---|
| 4,534,364 A | 8/1985 | Lamoreux | |
| 4,665,899 A | 5/1987 | Farris et al. | |
| 4,799,497 A | 1/1989 | Riley, II | |
| D352,111 S | 11/1994 | Watkins | |
| 5,388,591 A * | 2/1995 | De Luca et al. | 600/592 |
| 5,582,189 A * | 12/1996 | Pannozzo | 128/898 |
| 6,846,270 B1 * | 1/2005 | Etnyre | 482/6 |

\* cited by examiner

*Primary Examiner*—Max F. Hindenburg
*Assistant Examiner*—Brian Szmal
(74) *Attorney, Agent, or Firm*—Nydegger & Associates

(57) ABSTRACT

A computerized system and method for establishing a posture correction exercise program requires observing the patient relative to a predetermined framework. This is done to identify postural mal-alignments for the patient that can be respectively referenced to a predetermined view plane (frontal; sagittal; and transverse planes) and graded according to their severity. Additionally, the patient's weight bearing sensations are obtained for use with the mal-alignment data. This data is then input to a computer where each mal-alignment is matched with an exercise to create the corrective exercise program. The corrective exercise program can then be edited to customize the program for the patient.

17 Claims, 3 Drawing Sheets

TABLE OF EXERCISES

| Abbr | Exercise |
|---|---|
| 3ptr | 3 Position Toe Raises |
| 45ns | 45 degree Neck Stretch |
| 90p | 90 Degree - 90 Degree Position |
| ac | Arm Circle |
| ac-af | Ankle Circles-Ankle Flexes |
| aco | Abdominal Contractions |
| acr | Abdominal Crunches |
| acsb | Abdominal Curls on Swiss Ball |
| alef | Arm and Leg Extension On All Fours |
| bal | Balance |
| besb | Back Extensions on Swiss Ball |
| bfob | Bridge Feet on Ball |
| bhp | Bridge Hamstring Pull |
| bkbs | Bridging Knee Ball Squeeze |
| ble | Bilateral Leg Extension |
| bob | Bridging on Swiss Ball |
| br | Bridging |
| btp | Big Toe Push |
| cc | Cat and Camel |
| chs | Counter Hamstring Stetch |
| cht | Chin Tucks |
| cws | Calf Wedge Stretch |
| db | Diaphragmatic Breathing |
| dcs | Doorway Chest Stretch |
| ef | Elbow Flies |
| el | Extended Lateral |
| eoh | Extensions On Heels |
| fas | Foot/Arch Stretch |
| ffgs | Figure Four Gluteal Stretch |
| fs | Forearm Stretch |
| gc | Gluteal Contractions |
| gls | Gluteal Stretch |
| gs | Groin Stretch |
| hc | Hamstring Curls |
| hd | Heel Drop |
| hfa | Hip Flexor Abdominals |
| hfl | Hip Flexor Lifts |
| hfs | Hip Flexor Stretch |
| hlol | Hand/Leg Opposite Lift |
| hlolsb | Hand Leg Opposite Lift on Swiss Ball |
| hlor | Hand/Leg Opposite Reach |
| hr | Hip Rotations |
| hs | Hip Shift |
| hss | Hamstring Strap Stretch |
| ih | Isometric Hip Abduction |
| itbs | ITB Stretch |
| itl | Inner Thigh Lift |
| kbs | Knee Ball Squeezes |
| kgs | Kneeling Gluteal Squeezes |
| khfs | Kneeling Hip Flexor Stretch |
| lac | Lower Abdominal Crunches |
| lec | Legs Extended Crunches |
| lesb | Leg Extension on Swiss Ball |
| lhts | Lateral Hip Twist Stretch |
| ls | Long Sitting |
| lt | Lower Trapezius |
| lts | Lateral Trunk Stretch |
| mar | Marching |
| mns | Medial Nerve Stretch |
| nea | Neck Extensions Active |
| neob | Neck Extension off Bed |
| nett | Neck Extension with Towel Traction |
| nfb | Neck Forward Bend |
| nr | Neck Rotation |
| nsb | Neck Side Bend |
| otl | Outer Thigh Leg Lift |
| pgs | Prone Gluteal Squeezes |
| phc | Prone Hamstring Curls |
| phs | Pike Hamstring Stretch |
| pi | Parallel Ironing |
| po | Pullovers |
| pr | Pelvic Rock |
| pro | Pelvic Rotation |
| prsb | Prone on Swiss ball |
| ps | Prayer Stretch |
| psb | Push-Up on Swiss Ball |
| pss | Prone Scapula Strengthening |
| pu | Press Ups |
| qr | Quadruped Rocking |
| rns | Radial Nerve Stretch |
| sa | Snow Angel |
| sbc | Shoulder Blade Contractions |
| sbp | Shoulder Blade Press |
| sbs | Shoulder Blade Squeeze |
| scht | Sitting Chin Tucks |
| se | Static Extension |
| ser | Shoulder External Rotation |
| sfb | Sitting Forward Bend |
| sfr | Standing Flexion Rotation |
| sft | Sitting Floor Twists |
| shps | Static Hip Stretch |
| shs | Sitting Hamstring Stretch |
| skbs | Standing Knee Ball Squeeze |
| sle | Single Leg Extensions |
| slr | Straight Leg Raises |
| sqc | Standing Quad Contractions |
| sqs | Standing Quad Stretch |
| sr | Shoulder Rolls |
| srs | Spinal Rotation Stretch |
| ssb | Supine on Swiss Ball |
| ssh | Shoulder Shrugs |
| ssq | Sitting Sequence |
| sths | Standing Hamstring Stretch |
| tc | Towel Curls |
| ts | Tricep Stretch |
| tsq | Towel Sequence |
| tt | Towel Traction |
| ttw | Trunk Twist |
| uns | Ulnar Nerve Stretch |
| wgs | Wall Groin Stretch |
| whs | Wall Hamstring Stretch |
| wp | Wall Presses |
| ws | Wall Sits |
| ww | Wall Wash |

Fig. 4

SYSTEM AND METHOD FOR IMPLEMENTING POSTURAL REALIGNMENT PROGRAMS

FIELD OF THE INVENTION

The present invention pertains generally to physical exercise programs. More particularly, the present invention pertains to exercise programs that are generated with the assistance of a computer. The present invention is particularly, but not exclusively, useful as a system and method for generating corrective exercise programs for improving a person's posture.

BACKGROUND OF THE INVENTION

Posture can be succinctly defined as being the position or carriage of the human body. More particularly, posture refers to the habitual or assumed disposition of the parts of the body when standing, sitting, etc. Anatomically, good posture is exhibited whenever the component parts of the body's musculoskeletal structure are in proper alignment with each other. It happens, however, not all persons have good posture.

The mal-alignments of body parts that manifest themselves as poor posture have long been considered to be a predisposing factor in causing injuries. Specifically, these injuries can cause acute and chronic pains that result from increased joint wear and tear, decreased efficiency, disuse atrophy of muscles, and abnormal muscle patterns caused by substitution. Suffice it to say that maintaining good posture is essential for good health.

Through the years, the mal-alignments (postural deviations) that contribute to poor posture have been generally defined with reference to particular view planes. Specifically, these view plans are: 1) the frontal plane, 2) the sagittal plane, and 3) the transverse plane. The frontal or coronal plane derives its name from the direction or the coronal suture of the skull. It is a vertical plane that extends through the body from side to side, and divides the body into front and back sections of equal weight. On the other hand, the sagittal plane derives its name from the sagittal suture of the skull. It is also a vertical plane and divides the body into right and left halves. Unlike the frontal and sagittal planes, the transverse plane is horizontal and divides the body into upper (cranial) and lower (caudal) halves. With reference to these respective planes, observable skeletal mal-alignments (postural deviations) can be measured and evaluated. As indicated above, however, observable skeletal mal-alignments will also indicate muscular dysfunctions. More specifically, as implied above, posture is a consequence of the musculoskeletal structure of the human body. Accordingly, although the skeletal structure of the body is more easily observed, the muscular system of the body also needs consideration.

Insofar as posture is concerned, the muscles of the body can be generally divided into two groups. More generally, this division is based on the functionality of the respective muscle groups. One group is the dynamic muscle group (i.e. muscles that actively contract to coordinate and control body movements) the other is the static muscle group (i.e. muscles that provide tonic muscle control). With poor body posture, it is known that the muscles of both groups are adversely affected. Specifically, the dynamic muscle group becomes weaker, while muscles of the static muscle group become shorter.

As recognized by persons skilled in the art, in addition to the mal-alignments (postural deviations) that can be observed relative to standardized view planes, a person's weight bearing sensations also provide valuable diagnostic data. Specifically, it is known that a person's weight bearing sensations, as perceived by their feet in a standing position, can be used to help qualify muscle function. Importantly, all this data can be collectively evaluated and used to prescribe a proper sequence of appropriate exercises for both the static and dynamic muscle groups. The object, of course, is to prescribe an exercise program that will effectively correct the mal-alignments (postural deviations) that contribute to poor posture.

It happens that the number and type of exercises that are useful for correcting body mal-alignments (postural deviations) are many and varied. Consequently, the selection and proper sequencing or ordering of exercises for an effective corrective exercise program can be difficult and time consuming. Moreover, subjective considerations such as the severity of a particular mal-alignment can greatly influence the content and implementation of a corrective exercise program.

In light of the above, it is an object of the present invention to provide a system with a computerized method for creating a corrective exercise program that quickly and efficiently selects a sequence of appropriate exercises for correcting a person's posture. Another object of the present invention is to provide a computerized method for creating a corrective exercise program that is based on subjective considerations such as the weight bearing sensations of the person and the severity of particular postural deviations (mal-alignments). Still another object of the present invention is to provide a method for creating a corrective exercise program that can be easily reviewed and verified. Yet another object of the present invention is to provide a system with a computerized method for creating a corrective exercise program that is easy to implement, simple to use and comparatively cost effective.

SUMMARY OF THE INVENTION

A system and method for electronically evaluating the posture of a patient for the purpose of establishing a corrective exercise program requires performing a so-called "active test" and then positioning the patient in a grided framework. While the patient is positioned in the framework, a record of the patient's observable deviations from a correct postural alignment (i.e. mal-alignments) is prepared. Specifically, the mal-alignments are recorded with reference to body-based view planes that include: a frontal plane; a sagittal plane; and a transverse plane. In addition to results of the active test and the mal-alignments that are observed relative to the view planes, subjective data is also obtained from the patient pertaining to their weight bearing sensations.

As indicated above, in accordance with the present invention, an evaluation of a patient's posture begins by giving the patient an active test. Specifically, this active test involves having the patient close his/her eyes while jogging in place for a period of time. The general direction, extent and nature of any deviational movement by the patient from his/her initial position is then recorded for use with other test results.

For purposes of the present invention, the grided framework preferably includes a vertically oriented planar backdrop that has grid lines for a plurality of horizontally oriented rows and a plurality of vertically oriented columns.

Additionally, the framework includes a vertically oriented plumb line that is distanced from the backdrop to allow the patient to be positioned between the backdrop and the plumb line.

To identify postural deviations relative to the sagittal plane, the patient stands in the framework with his/her sagittal plane substantially perpendicular to the backdrop (i.e. frontal plane substantially parallel to the backdrop). Anterior, frontal right, posterior, frontal left and transverse views can then be taken of the patient. To identify postural deviations relative to the frontal plane, the patient turns and stands in the framework with his/her sagittal plane substantially parallel to the backdrop. Left and right views can then be taken. Postural deviations in the transverse plane are best observed from an overhead, superior, view point. Data that has been obtained from a patient, pertaining to his/her weight bearing sensations and his/her mal-alignments relative to the view planes, can be directly input to a computer. Optionally, the collected data can be somehow recorded and subsequently input into the computer.

For the present invention, a computer is used to group mal-alignments (postural deviations) according to their view plane and within each view plane group, to then evaluate the mal-alignments for their severity. The mal-alignments are then placed in order within their respective view plane according to their severity. Next, the computer is used to compare the ordered mal-alignments with various physical exercises for the purpose of appropriately matching exercises with mal-alignments. Typically, there will be several exercises that are needed for the correction of each mal-alignment. In any event, once exercises have been identified and selected for the correction of a particular mal-alignment, they are sequenced according to the efficacy of the exercise. The result is a corrective exercise program that can be output from the computer.

In most instances, the sequencing of exercises in the corrective exercise program will be established, in a preferred order, to reduce postural deviations (mal-alignments) in the frontal plane, reduce postural deviations in the sagittal plane and, reduce postural deviations in the transverse plane. In general, postural deviations referenced to the frontal plane include anterior/posterior pelvic tilts, forward/backward head, knee recurvatum, glenohumeral anterior/posterior translation, exaggerated/decreased anteroposterior spinal curves, and trunk rotations. Further, postural deviations referenced to the sagittal plane include left/right head side bend, high/low shoulder, high/low iliac crest, knee valgus and varus, tibial rotation, foot hyperpronation/supination, calcaneal valgus and varus. Still further, postural deviations referenced to the transverse plane include head rotations, trunk rotations, shoulder internal rotation, scapulae abduction, medial/lateral patella position, and internal/external hip rotations.

Once the corrective exercise program is output from the computer, it can be subsequently varied and customized by a therapist for the particular person whose posture is being corrected. A report for the corrective exercise program is then prepared and automatically generated to memorialize the findings. The corrective exercise program is then sent to the patient in any of several ways, such as by mail (i.e., hard copy) or email, as well as by CD/DVD, VHS or Streamed Video.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a table of exercises for correcting postural deviations (mal-alignments).

DESCRIPTION OF THE PREFERRED EMBODIMENTS

Figure 1:
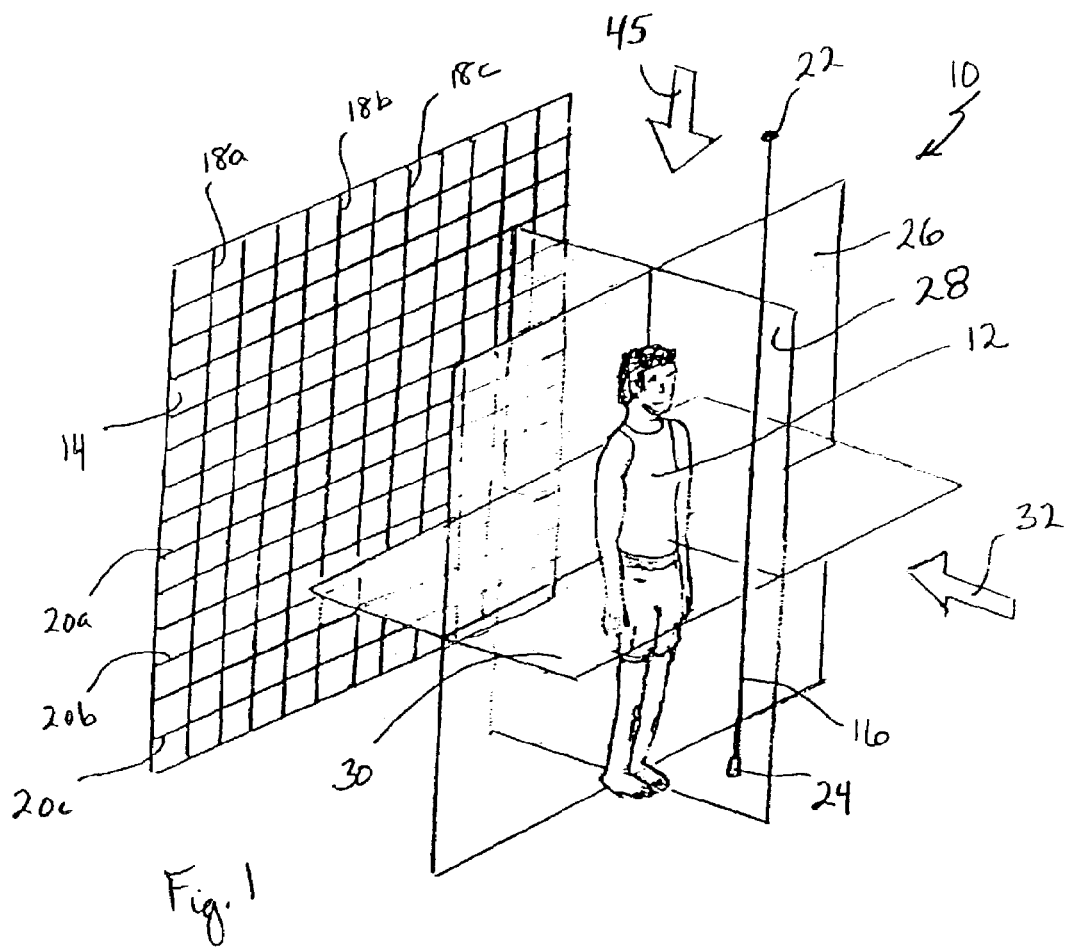
FIG. 1 is a perspective view of a patient/person standing in the framework of the present invention for the purpose of obtaining posture mal-alignment data.

Referring initially to FIG. 1, a framework for use with the present invention is shown, and is generally designated 10. As impliedly shown in FIG. 1, the intended use of the framework 10 is for the observation and measurement of postural deviations (mal-alignments) of a person/patient 12. Included in the framework 10 for these purposes are a planar backdrop 14 and a plumb line 16. More specifically, the backdrop 14 is oriented vertically and has a plurality of vertical lines 18, of which the lines 18a–c are exemplary. The backdrop 14 also has a plurality of horizontal lines 20, of which the lines 20a–c are exemplary. Together, the lines 18 and 20 form a grid-work. In front of this grid-work (backdrop 14) the plumb line 16 is hung from a point 22 on a structure (such as a ceiling, not shown) and is held taut by a weight 24. As shown, the plumb line 16 is distanced from the backdrop 14 to allow the person/patient 12 to stand between the backdrop 14 and the plumb line 16.

With specific reference to the person/patient 12, three different view planes can be identified. These are: a frontal plane 26, a sagittal plane 28 and a transverse plane 30. In general, the frontal plane 26 divides the person/patient 12 into front and back halves, while the sagittal plane 28 divides the person/patient 12 into right and left halves. The transverse plane 30, on the other hand, divides the person/patient 12 into upper (coronal) and lower (caudal) halves. Accordingly, when the person/patient 12 is standing in the framework 10, between the backdrop 14 and the plumb line 16, substantially as shown in FIG. 1, postural deviations (mal-alignments) can be observed relative to the vertical lines 18 and horizontal lines 20 on the backdrop 14. Specifically, as intended for the present invention, a therapist (not shown) will observe the person/patient 12 in the framework 10 from the perspective indicated by arrow 32. The postural deviations (mal-alignments) of the person/patient 12 can then be recorded on a posture evaluation chart that is shown and generally designated 34 in FIG. 2.

Figure 2:
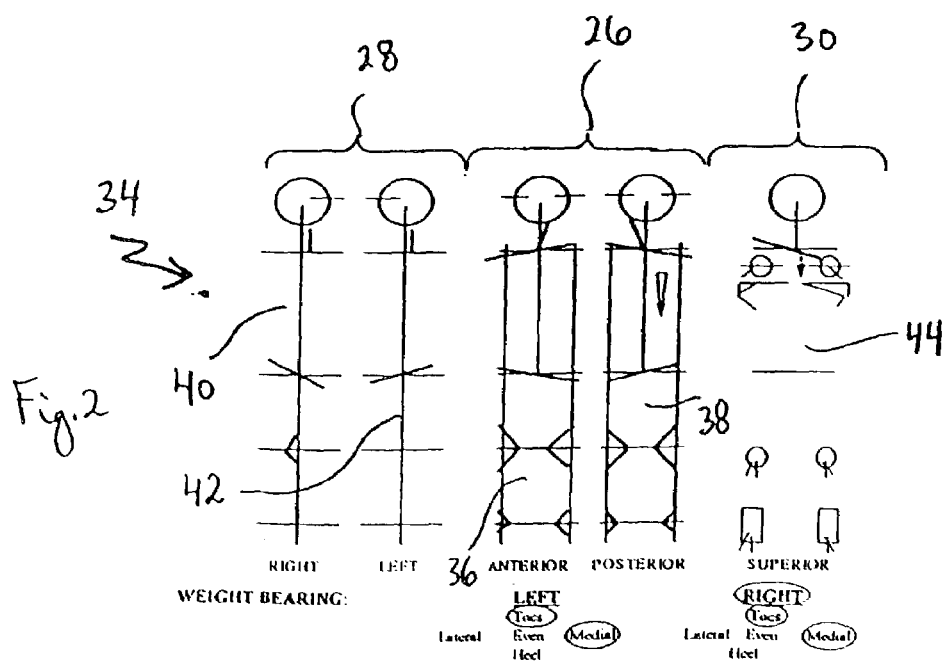
FIG. 2 is a posture evaluation chart for a patient/person representing commonly seen mal-alignments.

By cross referencing FIG. 1 with FIG. 2 it will be appreciated that direct visual observations of the person/patient 12 can be made from five different perspectives. Two of these perspectives pertain to the frontal plane 26, two pertain to the sagittal plane 28, and one perspective pertains to the transverse plane 30. For all five perspectives, the therapist views the person/patient 12 in the direction indicated by arrow 32. Specifically, insofar as views relative to the sagittal plane 28 are concerned, the person/patient 12 stands between the backdrop 14 and the plumb line 16, with the plumb line 16 in the sagittal plane 28. Then, facing the therapist, an anterior observation 36 of the person/patient 12 is made (i.e. with the person/patient 12 positioned as shown in FIG. 1). Also, when facing away from the therapist (i.e. with the person/patient 12 looking toward the backdrop 14) a posterior observation 38 is made.

To obtain views of the person/patient 12 relative to the frontal plane 26, the person/patient 12 turns so that the frontal plane 26 is substantially perpendicular to the backdrop 14. Also, the plumb line 16 should lie in the frontal plane 26. In this position, a right side observation 40 of the person/patient 12 can be made. By turning around to face the opposite direction, again with the frontal plane 26 substantially perpendicular to the backdrop 14, a left side observation 42 can also be made.

While the person/patient 12 is being observed, a superior observation 44 that is taken generally with reference to the transverse plane 30, is also made. Preferably, the superior observation 44 will be from a perspective taken in the direction of arrow 45. Additionally, subjective data concerning the weight bearing sensations of the person/patient 12 are also obtained. As indicated in FIG. 2, the data concerning the anterior observation 36, the posterior observation 38, the right side observation 40, the left side observation 42, the superior observation 44 and the weight bearing sensations are all recorded on the posture evaluation chart 34.

In addition to the data that is collected about the person/patient 12 with reference to the framework 10, it is also to be appreciated that data from an active test is also obtained for inclusion on the posture evaluation chart 34. As indicated above, the active test is performed by having the person/patient 12 close his/her eyes and then run or jog in place. The amount of time the person/patient 12 runs or jogs with their eyes closed is subjective. Most likely, however, the elapsed time for the active test will not be more than about ten or twenty seconds. In any event, whatever deviation the person/patient 12 experiences in movement from their initial location, while supposedly jogging in place with their eyes closed, is recorded for evaluation in conjunction with other data. Specifically, the data recorded from the active test will include the direction and extent of any deviational movement, as well as the time in the exercise at which such movement begins.

Figure 3:
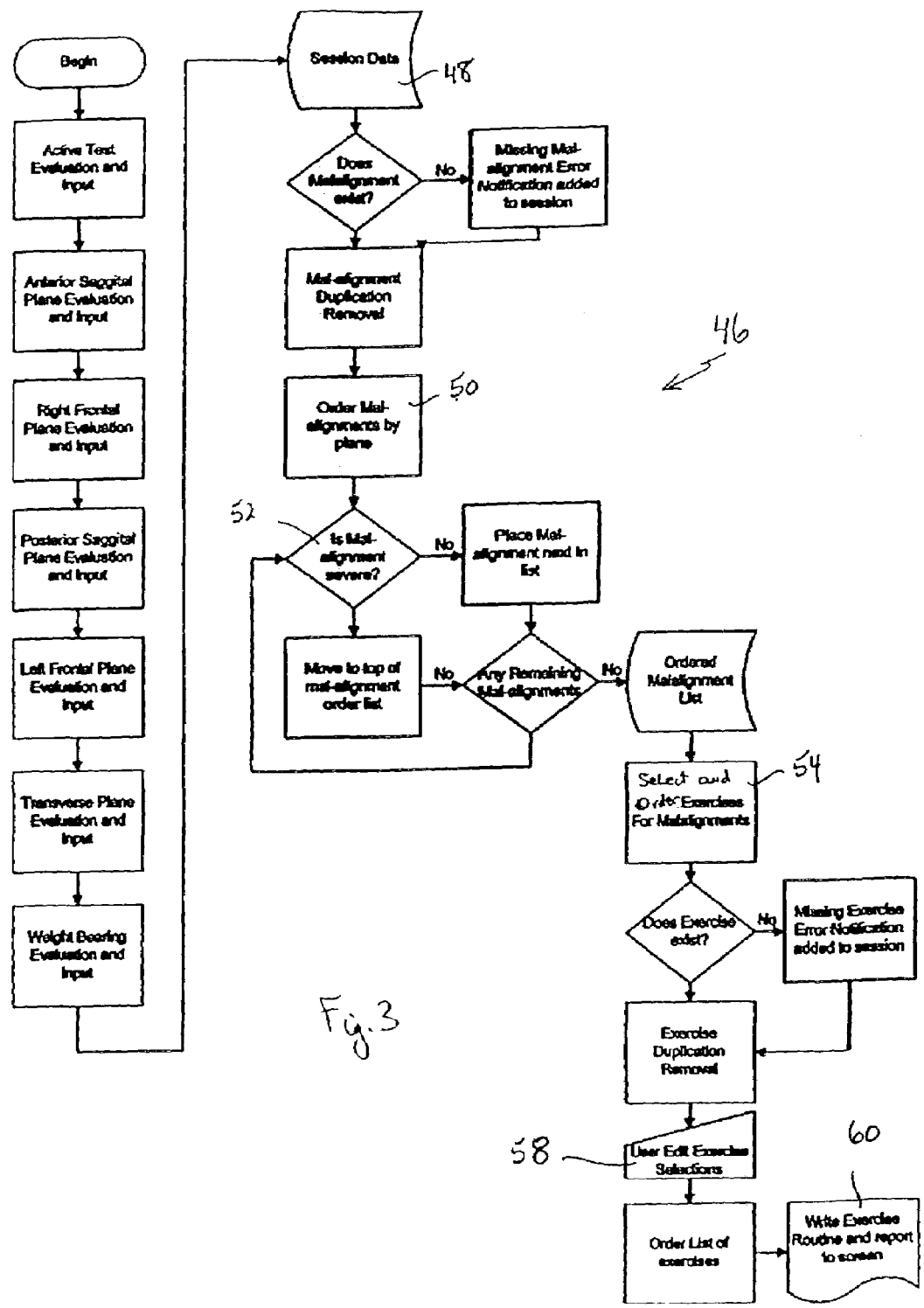
FIG. 3 is an operational flow chart for a computer that is useful for implementing the methods of the present invention.

FIG. 3 indicates that the data from the posture evaluation chart 34 can be used as input to a computer that will functionally follow an operational flow chart such as the one shown and generally designated 46 in FIG. 3. Optionally, the flow chart 46 can be used directly. In either case, the input of this data is indicated in the chart 46 by block 48. Action block 50 in chart 46 then indicates that the mal-alignments recorded in the postural evaluation chart 34 are ordered according to their respective view planes (i.e. frontal plane 26, sagittal plane 28, and transverse plane 30). Next, the inquiry block 52 and its associated functional blocks shown in FIG. 3 indicate that each mal-alignment is evaluated and ordered according to the severity of the particular mal-alignment. Once the mal-alignments have been organized, action block 54 in flow chart 46 indicates that appropriate exercises are selected. Typically, these exercises will be selected from the table 56 shown in FIG. 4 and will be arranged as a sequence of exercises that, in order, are designed to reduce postural deviations in the frontal plane 26, reduce postural deviations in the sagittal plane 28, and reduce postural deviations in the transverse plane 30.

In general, postural deviations (mal-alignments) referenced to the frontal plane 26 include anterior/posterior pelvic tilts, forward/backward head, knee recurvatum, glenohumeral anterior/posterior translation, exaggerated/decreased anteroposterior spinal curves, and trunk rotations. On the other hand, postural deviations (mal-alignments) that are referenced to the sagittal plane 28 include left/right head side bend, high/low shoulder, high/low iliac crest, knee valgus and varus, tibial rotation, foot hyperpronation/supination, calcaneal valgus and varus. Further, postural deviations (mal-alignments) that are referenced to the transverse plane 30 include head rotations, trunk rotations, shoulder internal rotation, scapulae abduction, medial/lateral patella position, and internal/external hip rotations.

As intended for the present invention, exercises will be automatically selected from those listed in table 56 (FIG. 4) for use in the corrective exercise program. Nevertheless, although the present invention is intended to be comprehensive and effective in the exercise selection process, the present invention also provides the user/therapist with the ability and opportunity to edit and modify the program when appropriate (see block 58 in chart 46). In each case, the result is an output 60 that can be used by a therapist to implement an effective program of exercises that will correct the posture of his/her patient/person 12.

While the particular System and Method for Implementing Postural Realignment Programs as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for electronically evaluating the posture of a patient to establish a corrective exercise program, the method comprising the steps of:

positioning the patient in a framework;

identifying postural deviations relative to the framework;

generating data for each postural deviation, wherein the data is characteristic of the postural deviation referenced to a predetermined view plane;

inputting the data to a computer for comparing the input data with a plurality of physical exercises corresponding to the respective view plane;

selecting exercises for inclusion in a corrective exercise program; and implementing the corrective exercise program to correct the posture of the patient.

2. A method as recited in claim 1 wherein the generating step further comprises the step of obtaining data from the patient pertaining to their weight bearing sensations and from the performance of an active test.

3. A method as recited in claim 1 wherein the predetermined view plane is one of a plurality of view planes which comprise:

a frontal plane;

a sagittal plane; and a transverse plane.

4. A method as recited in claim 3 further comprising the step of sequencing exercises in the corrective exercise program to, in order, reduce postural deviations in the frontal plane, reduce postural deviations in the sagittal plane and, reduce postural deviations in the transverse plane.

5. A method as recited in claim 3 wherein the framework comprises:

a vertically oriented backdrop, the backdrop including grid lines for a plurality of horizontally oriented rows and grid lines from a plurality of vertically oriented columns; and a vertically oriented plumb line lying substantially in the sagittal plane and distanced from the backdrop to allow positioning of the patient between the backdrop and the plumb line.

6. A method as recited in claim 3 wherein postural deviations referenced to the frontal plane include anterior/posterior pelvic tilts, forward/backward head, knee recurvatum, glenohumeral anterior/posterior translation, exaggerated/decreased anteroposterior spinal curves, and trunk rotations.

7. A method as recited in claim 3 wherein postural deviations referenced to the sagittal plane include left/right head side bend, high/low shoulder, high/low iliac crest, knee valgus and varus, tibial rotation, foot hyperpronation/supination, calcaneal valgus and varus.

8. A method as recited in claim 3 wherein postural deviations referenced to the transverse plane include head rotations, trunk rotations, shoulder internal rotation, scapulae abduction, medial/lateral patella position, and internal/external hip rotations.

9. A method for manipulating mal-alignment data for use in establishing a corrective exercise program for a patient which comprises the steps of:
    observing the patient relative to a predetermined framework to generate mal-alignment data for the patient corresponding to mal-alignments exhibited by the patient;
    inputting the observed mal-alignment data into a computer;
    electronically classifying the mal-alignment data according to severity;
    electronically ordering the mal-alignment data according to classification;
    electronically matching each mal-alignment in the mal-alignment data with an exercise to create a corrective exercise program;
    editing the corrective exercise program to customize the program for the patient; and
    implementing the corrective exercise program to correct the mal-alignments.

10. A method as recited in claim 9 further comprising the step of referencing the mal-alignment data to a respective predetermined view plane in a plurality of view planes which comprises:
    a frontal plane;
    a sagittal plane; and
    a transverse plane.

11. A method as recited in claim 10 further comprising the step of obtaining data from the patient pertaining to their weight bearing sensations for use with the mal-alignment data.

12. A method as recited in claim 11 further comprising the step of sequencing exercises in the corrective exercise program to, in order, reduce mal-alignments in the frontal plane, reduce mal-alignments in the sagittal plane and, reduce mal-alignments in the transverse plane.

13. A method as recited in claim 11 wherein mal-alignments referenced to the frontal plane include anterior/posterior pelvic tilts, forward/backward head, knee recurvatum, glenohumeral anterior/posterior translation, exaggerated/decreased anteroposterior spinal curves, and trunk rotations; wherein mal-alignments referenced to the sagittal plane include left/right head side bend, high/low shoulder, high/low iliac crest, knee valgus and varus, tibial rotation, foot hyperpronation/supination, calcaneal valgus and varus; and further wherein mal-alignments referenced to the transverse plane include head rotations, trunk rotations, shoulder internal rotation, scapulae abduction, medial/lateral patella position, and internal/external hip rotations.

14. A method as recited in claim 10 wherein the observing step is accomplished using a framework which comprises:
    a vertically oriented backdrop, the backdrop including grid lines for a plurality of horizontally oriented rows and grid lines from a plurality of vertically oriented columns; and
    a vertically oriented plumb line lying substantially in the sagittal plane and distanced from the backdrop to allow positioning of the patient between the backdrop and the plumb line.

15. A system for electronically evaluating the posture of a patient to establish a corrective exercise program which comprises:
    a grided framework for identifying postural deviations of the patient relative to the framework;
    means for generating data for each postural deviation, wherein the data is characteristic of the postural deviation referenced to a predetermined view plane, and for obtaining data from the patient pertaining to their weight bearing sensations;
    electronic means for inputting the data to a computer for comparing the input data with a plurality of physical exercises corresponding to the respective view plane;
    computer means for selecting exercises for inclusion in a corrective exercise program; and
    means for implementing the corrective exercise program to correct the posture of the patient.

16. A system as recited in claim 15 wherein the predetermined view plane is one of a plurality of view planes include a frontal plane, a sagittal plane, and a transverse plane; and wherein the computer means further comprises a means for sequencing exercises in the corrective exercise program to, in order, reduce postural deviations in the frontal plane, reduce postural deviations in the sagittal plane and, reduce postural deviations in the transverse plane.

17. A system as recited in claim 15 wherein the framework comprises:
    a vertically oriented backdrop, the backdrop including grid lines for a plurality of horizontally oriented rows and grid lines from a plurality of vertically oriented columns; and
    a vertically oriented plumb line lying substantially in the sagittal plane and distanced from the backdrop to allow positioning of the patient between the backdrop and the plumb line.

* * * * *